US009996889B2

(12) United States Patent
Gotz et al.

(10) Patent No.: US 9,996,889 B2
(45) Date of Patent: Jun. 12, 2018

(54) IDENTIFYING GROUP AND INDIVIDUAL-LEVEL RISK FACTORS VIA RISK-DRIVEN PATIENT STRATIFICATION

(71) Applicant: INTERNATIONAL BUSINESS MACHINES CORPORATION, Armonk, NY (US)

(72) Inventors: David H. Gotz, Purdys, NY (US); Pei-Yun S. Hsueh, Hawthorne, NY (US); Jianying Hu, Bronx, NY (US); Jimeng Sun, White Plains, NY (US)

(73) Assignee: International Business Machines Corporation, Armonk, NY (US)

( * ) Notice: Subject to any disclaimer, the term of this patent is extended or adjusted under 35 U.S.C. 154(b) by 265 days.

(21) Appl. No.: 13/632,659

(22) Filed: Oct. 1, 2012

(65) Prior Publication Data

US 2014/0095184 A1   Apr. 3, 2014

(51) Int. Cl.
*G06Q 50/22*       (2018.01)
*G06Q 10/06*       (2012.01)
*G06F 19/00*       (2018.01)

(52) U.S. Cl.
CPC ......... *G06Q 50/22* (2013.01); *G06F 19/3431* (2013.01); *G06F 19/3443* (2013.01); *G06Q 10/0635* (2013.01); *G06Q 10/0637* (2013.01)

(58) Field of Classification Search
CPC .... G06Q 50/22; G06Q 50/24; G06Q 10/0635; G06Q 10/0637; G06F 19/345; G06F 19/3443; G06F 19/3431
USPC ........................................................... 705/2
See application file for complete search history.

(56) References Cited

U.S. PATENT DOCUMENTS

| | | | |
|---|---|---|---|
| 6,653,140 B2 | 11/2003 | Otvos | |
| 7,054,758 B2 | 5/2006 | Gill-Garrison et al. | |
| 7,682,308 B2 | 3/2010 | Hendrich | |
| 8,010,295 B1 | 8/2011 | Magness et al. | |
| 8,078,407 B1 | 12/2011 | Brown | |
| 2004/0243362 A1* | 12/2004 | Liebman ............ G06F 19/3437 703/2 |
| 2008/0004915 A1 | 1/2008 | Brown | |
| 2008/0009684 A1 | 1/2008 | Corsetti et al. | |
| 2008/0147438 A1* | 6/2008 | Kil ................................... 705/2 |
| 2008/0275722 A1 | 11/2008 | Newell | |
| 2009/0018863 A1 | 1/2009 | Yoon et al. | |

(Continued)

OTHER PUBLICATIONS

Dash, M. et al., "Consistency-based search in feature selection", Artificial Intelligence, Mar. 2003, vol. 151, pp. 155-176.

(Continued)

*Primary Examiner* — Hiep V Nguyen
(74) *Attorney, Agent, or Firm* — Tutunjian & Bitetto, P.C.; Louis J. Percello

(57) ABSTRACT

Systems and methods for individual risk factor identification include identifying common risk factors for one or more risk targets from population data. Individuals are stratified into clusters based upon the common risk factors. A discriminability of each of the common risk factors is determined, using a processor, for a target cluster using individual data of the target cluster to provide re-ranked common risk factors as individual risk factors for the target cluster, such that the discriminability is a measure of how a risk factor discriminates its cluster from other clusters.

20 Claims, 3 Drawing Sheets

(56) References Cited

U.S. PATENT DOCUMENTS

| | | |
|---|---|---|
| 2009/0099888 A1 | 4/2009 | Nelson |
| 2009/0106004 A1 | 4/2009 | Edwards et al. |
| 2009/0132284 A1* | 5/2009 | Fey et al. .......................... 705/3 |
| 2010/0004947 A1 | 1/2010 | Nadeau et al. |
| 2010/0145953 A1 | 6/2010 | Charles et al. |
| 2010/0198611 A1* | 8/2010 | Ruoff et al. ...................... 705/2 |
| 2011/0093288 A1 | 4/2011 | Soto et al. |
| 2011/0144914 A1* | 6/2011 | Harrington .......... C12Q 1/6883 702/19 |
| 2013/0324785 A1 | 12/2013 | Bertram et al. |

OTHER PUBLICATIONS

Hall, M., "Correlation-based Feature Selection for Machine Learning", The University of Waikato thesis, Apr. 1999, (198 Pages).

Herbst et al., "The Effectiveness of Individual-, Group-, and Community-Level HIV Behavioral Risk-Reduction Interventions for Adult Men Who Have Sex with Men", American Journal of Preventive Medicine, Apr. 2007, pp. S38-S67.

Wilson et al., "Prioritizing Risk Factors to Identify Preventive Interventions for Economic Assessment", Bull World Heath Organ, New Zealand Jun. 1, 2011, pp. 88-96.

Yu et al., "Efficient Feature Selection via Analysis of Relevance and Redundancy", Journal of Machine Learning Research, vol. 5, Oct. 2004, pp. 1205-1224.

Yu et al., "Feature Selection for High-Dimensional Data . . . Filter Solution", Proceedings of the Twentieth International Conference on Machine Learning, Aug. 2003, (8 Pages).

Non-Final Office Action issued in U.S. Appl. No. 13/659,349 dated Sep. 18, 2014. (10 Pages).

Office Action dated Sep. 2, 2015 for U.S. Appl. No. 13/659,349.

\* cited by examiner

IDENTIFYING GROUP AND INDIVIDUAL-LEVEL RISK FACTORS VIA RISK-DRIVEN PATIENT STRATIFICATION

BACKGROUND

Technical Field

The present invention relates to risk factor identification, and more particularly to identifying group-level and individual-level risk factors via risk-driven patient stratification.

Description of the Related Art

As more clinical information with increasing diversity becomes available for analysis, a large number of features can be constructed and leveraged for predictive modeling. The ability to identify risk factors related to an adverse health condition (e.g., congestive heart failure) is very important for improving healthcare quality and reducing cost. The identification of risk factors may allow for the early detection of the onset of diseases so that aggressive intervention may be taken to slow or prevent costly and potentially life threatening conditions.

In personalized care management scenarios, it is common for two patients or groups of patients to have similar risk scores, but based on different risk factors. Conventionally, risk factor identification utilizes feature ranking methods to rank features that characterize the global utility of features. However, methods based on general population data will only yield common risk factors and do not address individual differences of patients.

SUMMARY

A method for individual risk factor identification includes identifying common risk factors for one or more risk targets from population data. Individuals are stratified into clusters based upon the common risk factors. A discriminability of each of the common risk factors is determined, using a processor, for a target cluster using individual data of the target cluster to provide re-ranked common risk factors as individual risk factors for the target cluster, such that the discriminability is a measure of how a risk factor discriminates its cluster from other clusters.

A method for individual risk factor identification includes identifying common risk factors for one or more risk targets from population data. Individuals are stratified into clusters based upon the common risk factors. The clusters are identified as one of a plurality of risk levels including at least one high-risk cluster and at least one low-risk cluster. A discriminability of each of the common risk factors is determined, using a processor, for a target cluster using individual data of the target cluster to provide re-ranked common risk factors as individual risk factors for the target cluster, such that the discriminability is a measure of how a risk factor discriminates its cluster from other clusters. The other clusters include at least one of other high-risk clusters, low-risk clusters, and a general population.

A method for individual risk factor identification includes identifying common risk factors for one or more risk targets from population data. Individuals are stratified into clusters based upon the common risk factors. The clusters are identified as one of a plurality of risk levels including at least one high-risk cluster and at least one low-risk cluster. A discriminability of each of the common risk factors is identified, using a processor, for a target cluster using individual data of the target cluster to provide re-ranked common risk factors, such that the discriminability is a measure of how a risk factor discriminates its cluster from other clusters. The other clusters include at least one of other high-risk clusters, low-risk clusters, and a general population. Each of the re-ranked common risk factors is validated using the individual data to provide individual risk factors for the target cluster by filtering out the common risk factors that do not indicate actual risk.

A system for individual risk factor identification includes a selection module configured to identify common risk factors for one or more risk targets from population data. A clustering module is configured to stratify individuals into clusters based upon the common risk factors. A ranking module is configured to determine, using a processor, a discriminability of each of the common risk factors for a target cluster using individual data of the target cluster to provide re-ranked common risk factors as individual risk factors for the target cluster, such that the discriminability is a measure of how a risk factor discriminates its cluster from other clusters.

A system for individual risk factor identification includes a selection module configured to identify common risk factors for one or more risk targets from population data. A clustering module is configured to stratify individuals into clusters based upon the common risk factors. A group identification module is configured to identify the clusters as one of a plurality of risk levels including at least one high-risk cluster and at least one low-risk cluster. A ranking module is configured to determine, using a processor, a discriminability of each of the common risk factors for a target cluster using individual data of the target cluster to provide re-ranked common risk factors as individual risk factors for the target cluster, such that the discriminability is a measure of how a risk factor discriminates its cluster from other clusters. The other clusters include at least one of other high-risk clusters, low-risk clusters, and a general population.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein.

DETAILED DESCRIPTION OF PREFERRED EMBODIMENTS

Figure 1:
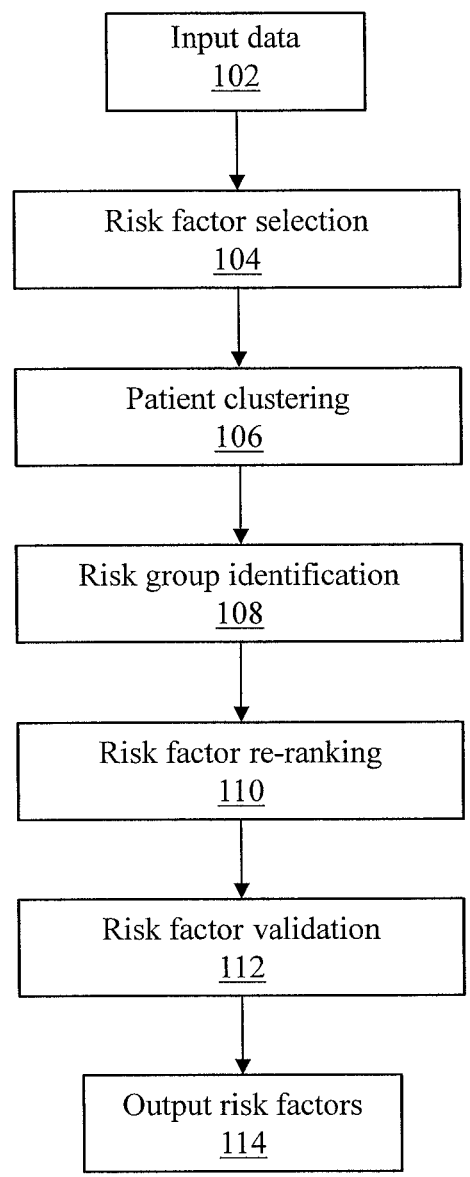
FIG. 1 is a block/flow diagram showing a high level overview of a system/method for individual risk factor identification in accordance with one illustrative embodiment.

In accordance with the present principles, systems and methods for identifying individual-level risk factors are provided. Individual data and population data may be received as input. Individual data may include data for a target group or cluster. In a preferred embodiment, the target cluster is representative of a target individual or patient, e.g., to be treated or examined. Individual data may include, e.g., electronic health records, questionnaire data, genetic information, etc.

Using population data, common (i.e., global) risk factors for one or more specific risk targets (e.g., diabetes) are identified. Preferably, each risk factor is identified as being positively or negatively correlated with the risk target. Using the identified risk factors, patients from the population data are stratified into clusters. Stratifying patients into clusters may include applying, e.g., hierarchical clustering, k-means clustering, 2-step clustering, etc. Other methods of clustering are also contemplated. Each cluster is identified as being high-risk or low-risk. This may be based on the proportion of at-risk patients in each cluster.

The identified risk factors are re-ranked based upon the importance of each risk factor to the target cluster. The importance can be quantified for each risk factor as how much the risk factor discriminates its cluster (i.e., the target cluster) from the remaining population. A number of comparison configurations may be applied. In one embodiment, the target cluster may be compared against all other high-risk clusters. In another embodiment, the target cluster may be compared against all low-risk clusters. In still another embodiment, the target cluster may be compared against the general population. Other comparison configurations are also contemplated. Using one of the comparison configurations, discriminability may be determined. In one embodiment, discriminability may be determined by calculating how much each factor contributes to the training of a classifier. In another embodiment, discriminability may be determined by calculating how much the distribution of each factor differs in the target cluster as compared to the pertinent clusters for the selected comparison configuration.

Risk factors that do not indicate actual risk at the local level may be filtered out. The remaining risk factors are outputted as individual risk factors. The individual risk factors identify the primary risk factors for a target cluster or target patient. Advantageously, the individual risk factors may be utilized to, e.g., customize a personalized care management process or may be displayed for clinical decision support at the point-of-care or for patient education.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing. Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks. The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Referring now to the drawings in which like numerals represent the same or similar elements and initially to FIG. 1, a block/flow diagram showing a system/method for a high-level overview of individual risk factor identification 100 is illustratively depicted in accordance with one embodiment. In block 102, data is received as an input, including individual data and population data. Individual data includes data for a cluster of one or more individuals (e.g., patients), which may be representative of a target individual. Individual data may include, e.g., electronic medical records (e.g., diagnosis, lab results, medication, hospitalization records, etc.), personal lifestyle questionnaire data, personal genetic information, and the like.

In block 104, population data is used to identify common risk factors for a specific risk target (e.g., diabetes, congestive heart failure, etc.). The identified risk factors are preferably ranked based on global utility. For each identified risk factor, it is indicated whether they are positively or negatively correlated with the specific risk target.

In block 106, individuals (from the population data) are stratified into clusters based on the identified risk factors. The objective is to group individuals into clusters to reflect the differences in their characteristics. Patients within the same cluster are exposed to similar risk factors than those in other clusters.

In block 108, risk groups are identified from the clusters. High and low risk groups are identified based upon the proportion of at-risk patients in each cluster. In block 110, the set of identified risk factors identified in block 104 are re-ranked based on how much each risk factor discriminates its cluster from other clusters.

In block 112, risk factors are validated. Risk factors that do not indicate actual risk at the individual/group level are filtered out. In block 114, individual/group risk factors are outputted. The individual/group risk factors may be used, e.g., in a personalized care management process or may be displayed in a user interface or dashboard.

Figure 2:
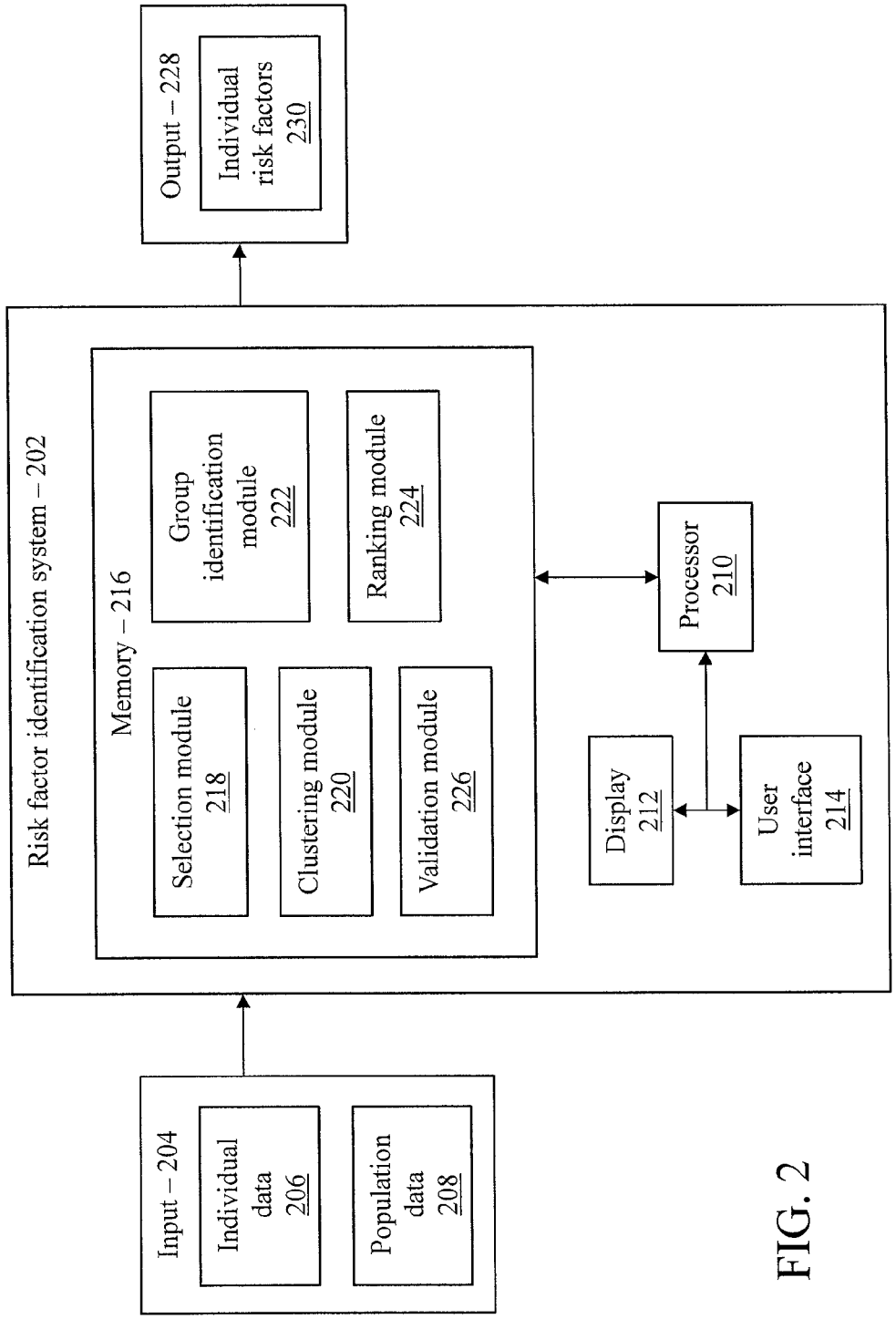
FIG. 2 is a block/flow diagram showing a system for individual risk factor identification in accordance with one illustrative embodiment.

Referring now to FIG. 2, a block/flow diagram showing a system 200 for individual risk factor identification is illustratively depicted in accordance with one embodiment. The system 200 identifies risk factors for a cluster of individuals (e.g., patients). The cluster of individuals may preferably represent a target individual, such as, e.g., a particular patient to be examined. The system may include a workstation or console 202 from which procedures (e.g., medical examination) may be performed. The system 202 preferably includes one or more processors 210 and memory 216 for storing programs, applications and other data. It should be understood that the functions and components of system 200 may be integrated into one or more workstations or systems.

System 202 may include one or more displays 212 for viewing. The display 212 may also permit a user (e.g., physician, care coordinator, care giver, etc.) to interact with the system 202 and its components and functions. This is further facilitated by a user interface 214, which may include a keyboard, mouse, joystick, or any other peripheral or control to permit user interaction with the system 202.

System 202 receives input 204, which may include individual data 206 and population data 208. Individual data 206 may include data for a cluster of individuals, which may represent a target individual. For example, individual data 206 may include electronic medical records such as diagnoses, lab results, medication and hospitalization records, questionnaire data (e.g., personal lifestyle questionnaire), personal genetic information, etc. for a cluster of individuals. Other data are also contemplated.

Memory 216 may include selection module 218 configured to identify common (i.e., global) risk factors for one or more specific risk targets (e.g., diabetes, congestive heart failure, etc.) from population data 208. Risk targets are preferably received as an input 204. Selection module 218 may identify common risk factors using feature selection based upon, e.g., filters, wrappers, embedded, and ensemble voting. Filter based feature selection may include, e.g., scoring with statistical measures (chi-squared ($X2$), etc.), scoring with information theoretic measure (information gain, symmetrical uncertainty, etc.), scoring with feature contribution evaluation (oneR, random forest, relief-f, etc.), and the like. Wrapper based feature selection may include, e.g., wrappers with search methods (breadth first search, exhaustive search, forward search, backward search, hill-climbing search, etc.), wrappers with feature subset quality checking measures (correlation-based feature selection, consistency-based feature selection, etc.), and the like. Embedded based feature selection may be based on, e.g., decision trees, logistic regression, support vector machine, etc. Ensemble voting based feature selection selects those features that have more than one selector voted on. Other selection methods and configurations are also contemplated.

The selection module 218 ranks identified common risk factors using objective functions that characterize the global utility (i.e., importance) of the risk factors. Preferably, the selection module 218 identifies whether a risk factor is positively or negatively correlated with a specific risk target. For example, positively correlated risk factors for congestive heart failure may include age, smoking, blood pressure, alcohol consumption, etc., while negatively correlated risk factors for congestive heart failure may include high-density lipoprotein cholesterol, diet control, etc. The selection module 218 selects the top n risk factors, where n is any positive integer.

Memory 216 may also include clustering module 220 configured to stratify individuals into clusters using the common risk factors selected by selection module 218. In one embodiment, clustering module 220 applies hierarchical clustering with a known number of clusters k. Each individual may be assigned as its own cluster. The distance between each cluster represents the similarity based on the common risk factors. The distance may be represented as a distance metric, such as, e.g., Euclidean distance, Mahalanobis distance, Manhattan distance, etc. Other metrics are also contemplated. The closest pair of clusters (i.e., most similar) are merged into a single cluster. Cluster similarity may be based upon, e.g., single-link clustering, complete-link cluster, average-link clustering, etc. Distances between the newly formed cluster and the remaining clusters are then computed and the process is repeated until a specified number of clusters k remains. It is to be understood that clustering module 220 may apply other clustering methods, such as, e.g., k-means cluster, 2-step cluster, etc. Clustering module 220 may apply soft assignment techniques, such that individuals may be assigned to multiple clusters.

Memory 216 also includes group identification module 222 configured to identify the clusters at a plurality of risk levels. In a preferred embodiment, clusters are identified as high-risk and low-risk clusters. Risk levels of a cluster may be identified based upon the proportion of at-risk individuals in each cluster. In one embodiment, clusters are identified as high-risk where the proportion of at-risk individuals is above a predefined risk threshold (e.g., a cluster with a proportion of at-risk individuals >0.7 is identified as high-risk). At-risk individuals may be identified using a classifier previously trained from a similar patient pool to assign risk scores to each individual. Based on the risk score, each individual of the cluster may be identified as at-risk (e.g., an individual with a risk score >0.5 is identified as at-risk). In another embodiment, the risk status (e.g., at-risk) of each individual is known, such as, e.g., in a training phase. Other configurations of group identification module 222 to identify clusters at a plurality of risk levels are also contemplated.

Memory 216 includes ranking module 224 configured to re-rank the common risk factors (from selection module 218) based upon how important each risk factor is to its particular risk cluster. The importance can be quantified as how much a risk factor discriminates its local cluster from other clusters. The discriminability of each risk factor for its cluster may be measured by comparing its cluster (i.e., the target cluster) with other clusters or individuals based on a number of different comparison configurations. In one embodiment, the target cluster is compared with all other high-risk clusters. In another embodiment, the target cluster is compared with all low-risk clusters. In yet another embodiment, the target cluster is compared with the general population. Other comparison configurations are also contemplated.

Based upon a comparison configuration, risk factor discriminability is measured. In one embodiment, risk factor discriminability is measured by calculating how much each risk factor contributes to the training of a classifier (e.g., logistic regression model, support vector machine, etc.) for a particular comparison configuration, while accounting for the bias introduced by the classifier. The classifier may be trained to distinguish the target cluster from the other clusters specified in the comparison configuration. Preferably, the classifier is trained via, e.g., cross validation. The feature contribution information (i.e., weightings) exhibited in the training process (e.g., forward selection, backward selection, etc.) are used to rank features for selection purposes. The weightings of each risk factor learned in the classifier training indicate the importance of each of the risk factors in discriminating the target cluster from other clusters. The best-performing subset of features is selected.

In another embodiment, risk factor discriminability is measured by calculating how much the distribution of each risk factor differs between the target cluster and the clusters or individuals pertaining to the selected comparison configuration. The distribution may be based upon a frequency count of each risk factor using statistical methods (e.g., chi-squared (X2), log likelihood ratio (LLR), etc.) and information theoretic methods (e.g., point wise mutual information (PMI), information gain (IG), etc.). The distributions of risk factors may be compared based on, e.g., the sign test, Wilcoxon signed-rank test, Spearman's rank-order correlation, Kendall's tau correlation, etc. Other methods are also contemplated.

Preferably, the best combination of the comparison configuration and discriminability measure is applied to provide local risk factors (i.e., re-ranked common risk factors). The best combination may represent the combination that results in a local risk factor ranking that discerns the at-risk cluster from other clusters. The best combination may be determined by comparing the re-ranked common risk factors for each combination with the ranked common risk factors determined by selection module 218. For example, goodness-of-fit measures may be used to compare re-ranked common risk factors with the ranked common risk factor. Other measures of comparing risk factor rankings are also contemplated.

Memory 216 may include validation module 226 configured to filter out re-ranked common risk factors that do not indicate actual risk for the target cluster to provide individual risk factors for the target cluster. The validation module 226 may be implemented as a set of rules to filter out common risk factors that may be discriminative of the target cluster, but its inclusion does not indicate risk increase for the specific risk target. For example, high HDL may actually indicate risk reduction for patient; however this is not a risk factor. In another embodiment, the positive/negative correlation of a particular risk factor (identified by the selection module 218) is compared against the data in the target individual/risk group. Other filtering criteria are also contemplated.

The risk factor identification system 202 may provide output 228. Output 228 may include individual risk factors 230 for a cluster of individuals, which may represent a target individual or patient. In one application, individual risk factors 230 may be applied in a personal care management process for, e.g., clinical decision support at the point-of-care. In another application, individual risk factors 230 may be displayed using display 212 and/or user interface 214 to, e.g., customize healthcare plans or tailor patient education. Other applications are also contemplated.

Figure 3:
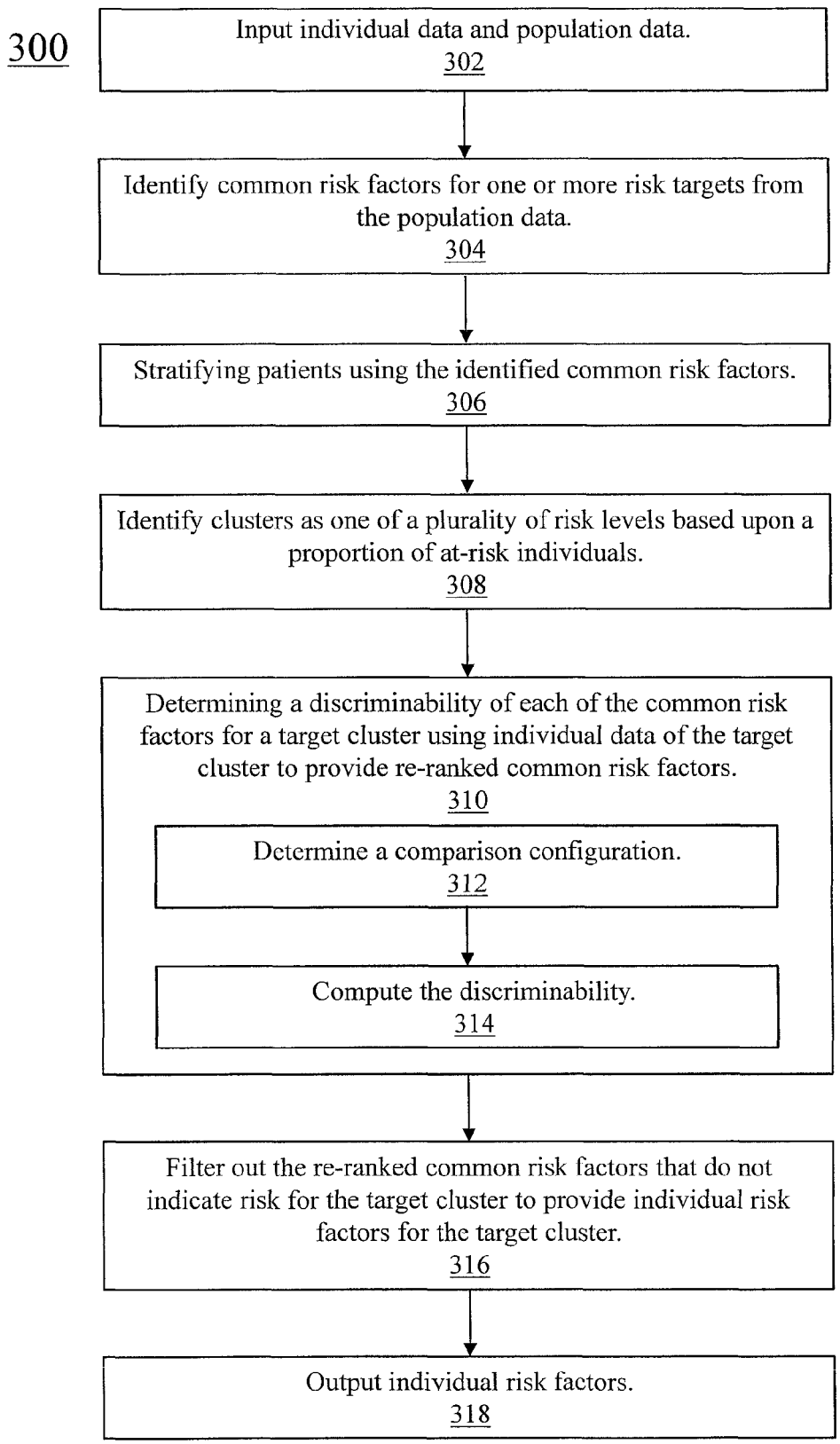
FIG. 3 is a block/flow diagram showing a method for individual risk factor identification in accordance with one illustrative embodiment.

Referring now to FIG. 3, a flow diagram showing a method for risk factor identification 300 is illustratively depicted in accordance with one embodiment. In block 302, individual data and population data are inputted. Individual data may include data for a cluster of individuals (e.g., patients). Preferably, the cluster of individuals is representative of a target individual or patient. Individual data may include, for example, electronic medical records (e.g., diagnosis, lab results, medication, hospitalization records), questionnaire data (e.g., personal lifestyle questionnaire), genetic information, and the like.

In block 304, common risk factors are identified and ranked for one or more risk targets from the population data. Risk targets, such as, e.g., diabetes, congestive heart failure, etc., are preferably received as an input. Common risk factor identification may be, e.g., filter based, wrapper based, embedded based, ensemble voting based, etc. Risk factors are ranked using objective functions that characterize global utility of the risk factors. In a preferred embodiment, the positive or negative correlation of each risk factor is identified for the specific risk target. The top n risk factors are selected, where n is any positive integer. Other methods of common risk factor identification and ranking are also contemplated.

In block 306, individuals are stratified into clusters using the identified common risk factors. Clustering may include applying hierarchical clustering, k-means clustering, 2-step clustering, etc. Other clustering methods are also contemplated. The clustering methods may be based on distance metrics, such as, e.g., the Euclidean distance, Mahalanobis distance, Manhattan distance, etc. Inherently, patients within a cluster are exposed to similar risk factors than those patients in other clusters.

In block 308, clusters are identified as one of a plurality of risk levels. Preferably, the plurality of risk levels includes a high-risk cluster and a low-risk cluster. Clusters may be identified based upon the proportion of at-risk patients in each cluster. In one embodiment, high-risk clusters are identified as clusters with a proportion of at-risk patients greater than a predefined risk threshold. At-risk patients may be determined using a classifier to assign a risk score to each individual. Classifiers may be previously trained using a similar patient pool. Risk scores may be used to determine whether an individual is at-risk (e.g., an individual with a risk score >0.5 is identified as at-risk). In another embodiment, the risk status of individuals may already be known (e.g., in a training phase). Other methods of cluster risk identification are also contemplated.

In block 310, a discriminability of each of the common risk factors may be determined for a target cluster using the individual data of the target cluster to provide re-ranked common risk factors. The discriminability may be determined such that the discriminability is a measure of how a risk factor discriminates its cluster (i.e., the target cluster) from other clusters. The discriminability may be measured using a number of different comparison configurations. In block 312, a comparison configuration is selected. In one embodiment, the target cluster is compared with all other high-risk clusters. In another embodiment, the target cluster is compared with all low-risk clusters. In yet another embodiment, the target cluster is compared with the general population. Other comparison configurations are also contemplated.

Based upon the comparison configuration, in block 314, the discriminability of each risk factor may be determined. In one embodiment, discriminability is measured by calculating how much each risk factor contributes to the training of a classifier, such as, e.g., a logistic regression model, a support vector machine, etc. The classifier is preferably trained to distinguish the target cluster from the other clusters as specified in the comparison configuration. Training may be performed by, e.g., cross validation. The weightings learned in the classifier training are used to rank features for selection purposes. The weightings indicate the importance of each risk factor to its cluster (i.e., its discriminability). The best-performing subset of features is selected. In another embodiment, discriminability may be measured by calculating how much the distribution of each risk factor differs in the target cluster and pertinent clusters selected in the comparison configuration. A number of methods may be applied, such as statistical methods (e.g., chi-square statistics (X2), log-likelihood ratio (LLR), etc.) and information theoretic methods (e.g., point-wise mutual information (PMI), etc.). Other methods of determining discriminability are also contemplated.

Preferably, the best combination of the comparison configuration (block 312) and discriminability measure (block 314) is applied to provide re-ranked common risk factors. The best combination may represent the combination that results in re-ranked common risk factors that discern the at-risk target cluster from other clusters. The best combination may be determined by comparing re-ranked common risk factors for each combination with the ranked common risk factors determined in block 304. In one embodiment, goodness-of-fit measures may be used to compare re-ranked risk factors with the common risk factors. Other measures of comparing risk factor rankings are also contemplated.

In block 316, the re-ranked common risk factors are filtered out that do not indicate actual risk for the target cluster to provide individual risk factors for the target cluster. Preferably, a set of rules are used to filter out risk factors may be discriminative of the target cluster, but does not indicate risk increase in the risk target.

In block 318, individual risk factors are outputted for the target cluster. The target cluster preferably represents a target individual or patient. The individual risk factors may be, e.g., incorporated in a personalized care management process or may be displayed for, e.g., clinical decisions at the point-of-care or patient education.

Having described preferred embodiments of identifying group and individual level risk factors via risk-driven patient stratification (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A method for individual risk factor identification, comprising:
identifying common risk factors for one or more risk targets from population data;
stratifying individuals into clusters based upon the common risk factors, wherein a distance between each cluster represents a similarity based upon the common risk factors, and wherein a closest pair of clusters is iteratively merged into a single cluster until a threshold condition is reached;
determining, using a processor, a discriminability of each of the common risk factors for a target cluster using individual data of the target cluster to provide re-ranked common risk factors as individual risk factors for the target cluster, such that the discriminability is a quantitative measure of how a risk factor discriminates its cluster from other clusters; and
customizing and performing, using a personalized user interface and dashboard display operatively coupled to at least one hardware based care-management machine, a personalized hardware-based care management process by controlling the at least one hardware based care-management machine for personalized treatment of a particular individual, the personalized user interface and dashboard display comprising a customized graphical user interface (GUI) configured for customizing healthcare plans, tailored to the particular individual based on the individual risk factors determined by the identifying common risk factors, the stratifying individuals into clusters and the re-ranked common risk factors, and for providing real-time clinical decision support at a point-of-care for the particular individual.

2. The method as recited in claim 1, further comprising identifying the clusters as one of a plurality of risk levels.

3. The method as recited in claim 2, wherein the plurality of risk levels include at least one low-risk cluster and at least one high-risk cluster.

4. The method as recited in claim 3, wherein determining the discriminability for each risk factor for the target cluster includes comparing risk factors for the target cluster with risk factors for at least one of: other high-risk clusters, low-risk clusters, and a general population.

5. The method as recited in claim 2, wherein identifying the clusters includes identifying the clusters as one of a plurality of risk levels based upon a proportion of at-risk individuals in each cluster.

6. The method as recited in claim 5, wherein at-risk individuals are identified based upon a risk score.

7. The method as recited in claim 6, wherein the risk score is assigned using a classifier.

8. The method as recited in claim 1, wherein determining the discriminability includes determining an amount each risk factor contributes to training a classifier for a particular comparison configuration while accounting for a bias introduced by the classifier.

9. The method as recited in claim 1, wherein determining the discriminability includes determining a difference in a frequency count-based distribution between each risk factor in the target cluster and the other clusters.

10. The method as recited in claim 1, further comprising validating each of the individual risk factors using the individual data by filtering out the common risk factors that do not indicate actual risk.

11. The method as recited in claim 1, wherein the individual data includes one or more of: diagnosis, lab results, medication, hospitalization records, questionnaire data and genetic information for the target cluster.

12. A method for individual risk factor identification, comprising:
   identifying common risk factors for one or more risk targets from population data;
   stratifying individuals into clusters based upon the common risk factors, wherein a distance between each cluster represents a similarity based upon the common risk factors, and wherein a closest pair of clusters is iteratively merged into a single cluster until a threshold condition is reached;
   identifying the clusters as one of a plurality of risk levels including at least one high-risk cluster and at least one low-risk cluster;
   determining, using a processor, a discriminability of each of the common risk factors for a target cluster using individual data of the target cluster to provide re-ranked common risk factors as individual risk factors for the target cluster, such that the discriminability is a quantitative measure of how a risk factor discriminates its cluster from other clusters, the other clusters including at least one of other high-risk clusters, low-risk clusters and a general population; and
   customizing and performing, using a personalized user interface and dashboard display operatively coupled to at least one hardware based care-management machine, a personalized hardware-based care management process by controlling the at least one hardware based care-management machine for personalized treatment of a particular individual, the personalized user interface and dashboard display comprising a customized graphical user interface (GUI) configured for customizing healthcare plans, tailored to the particular individual based on the individual risk factors determined by the identifying common risk factors the stratifying individuals into clusters, and the re-ranked common risk factors, and for providing real-time clinical decision support at a point-of-care for the particular individual.

13. The method as recited in claim 12, wherein identifying the clusters includes identifying the clusters as one of a plurality of risk levels based upon a proportion of at-risk individuals in each cluster.

14. The method as recited in claim 13, wherein at-risk individuals are identified based upon a risk score.

15. The method as recited in claim 14, wherein the risk score is assigned using a classifier.

16. The method as recited in claim 12, wherein determining the discriminability includes determining an amount each risk factor contributes to training a classifier for a particular comparison configuration while accounting for a bias introduced by the classifier.

17. The method as recited in claim 12, wherein determining the discriminability includes determining a difference in a frequency count-based distribution between each risk factor in the target cluster and the other clusters.

18. The method as recited in claim 12, further comprising validating each of the individual risk factors using the individual data by filtering out the common risk factors that do not indicate actual risk.

19. The method as recited in claim 12, wherein the individual data includes one or more of: diagnosis, lab results, medication, hospitalization records, questionnaire data and genetic information for the target cluster.

20. A method for individual risk factor identification, comprising:
   identifying common risk factors for one or more risk targets from population data;
   stratifying individuals into clusters based upon the common risk factors, wherein a distance between each cluster represents a similarity based upon the common risk factors, and wherein a closest pair of clusters is iteratively merged into a single cluster a threshold condition is reached;
   identifying the clusters as one of a plurality of risk levels including at least one high-risk cluster and at least one low-risk cluster;
   determining, using a processor, a discriminability of each of the common risk factors for a target cluster using individual data of the target cluster to provide re-ranked common risk factors, such that the discriminability is a quantitative measure of how a risk factor discriminates its cluster from other clusters, the other clusters including at least one of other high-risk clusters, low-risk clusters, and a general population;
   validating each of the re-ranked common risk factors using the individual data to provide individual risk factors for the target cluster by filtering out the common risk factors that do not indicate actual risk; and
   customizing and performing, using a personalized user interface and dashboard display operatively coupled to at least one hardware based care-management machine, a personalized hardware-based care management process by controlling the at least one hardware based care-management machine for personalized treatment of a particular individual, the personalized user interface and dashboard display comprising a customized graphical user interface (GUI) configured for customizing healthcare plans, tailored to the particular individual based on the individual risk factors determined by the identifying common risk factors, the stratifying individuals into clusters, and the re-ranked common risk factors, and for providing real-time clinical decision support at a point-of-care for the particular individual.

\* \* \* \* \*